United States Patent [19]

Schultz et al.

[11] Patent Number: 5,168,612

[45] Date of Patent: Dec. 8, 1992

[54] NEEDLE ELIMINATOR

[76] Inventors: Elliot P. Schultz, 186 NW. 108th Ave., Coral Springs, Fla. 33071; Raymond L. Sperry, 7194 Promenade Dr., Boca Raton, Fla. 33433

[21] Appl. No.: 731,159

[22] Filed: Jul. 16, 1991

[51] Int. Cl.⁵ .......................................... B23Q 41/00
[52] U.S. Cl. ..................................... 29/33 R; 128/919
[58] Field of Search .................... 29/33 R, 426.5, 650, 29/240, 564.3, 564.7, 564.1; 128/919; 604/199, 111; 206/370, 366, 210

[56] References Cited

U.S. PATENT DOCUMENTS

| | | | |
|---|---|---|---|
| 4,862,573 | 9/1989 | Kelson et al. | 29/240 |
| 4,921,491 | 5/1990 | Champ | 604/199 |
| 4,989,307 | 2/1991 | Sharpe | 29/240 |
| 5,038,929 | 8/1991 | Kubofcik | 206/210 |
| 5,076,178 | 12/1991 | Kohl et al. | 128/919 X |

FOREIGN PATENT DOCUMENTS 8810126 12/1988 PCT Int'l Appl. ................. 128/919

Primary Examiner—William Briggs
Attorney, Agent, or Firm—Malin, Haley, McHale, DiMaggio & Crosby

[57] ABSTRACT

A machine for destroying, disinfecting and collecting in safe, removable, disposable containers hypodermic needles and syringes containing medical contaminants. The device includes a compact housing which is easily portable, a shear housing containing removable and serviceable shear blades and a shear member. A safety container which includes a clear visual top is used and collects the destroyed needles and syringes in a container that can be subsequently readily disposed of. A low RPM high torque motor is used to greatly reduce the noise of operation of the device. A front observation window in the housing permits the viewer to determine how full the safety container is visually through the clear top of the safety container.

8 Claims, 3 Drawing Sheets

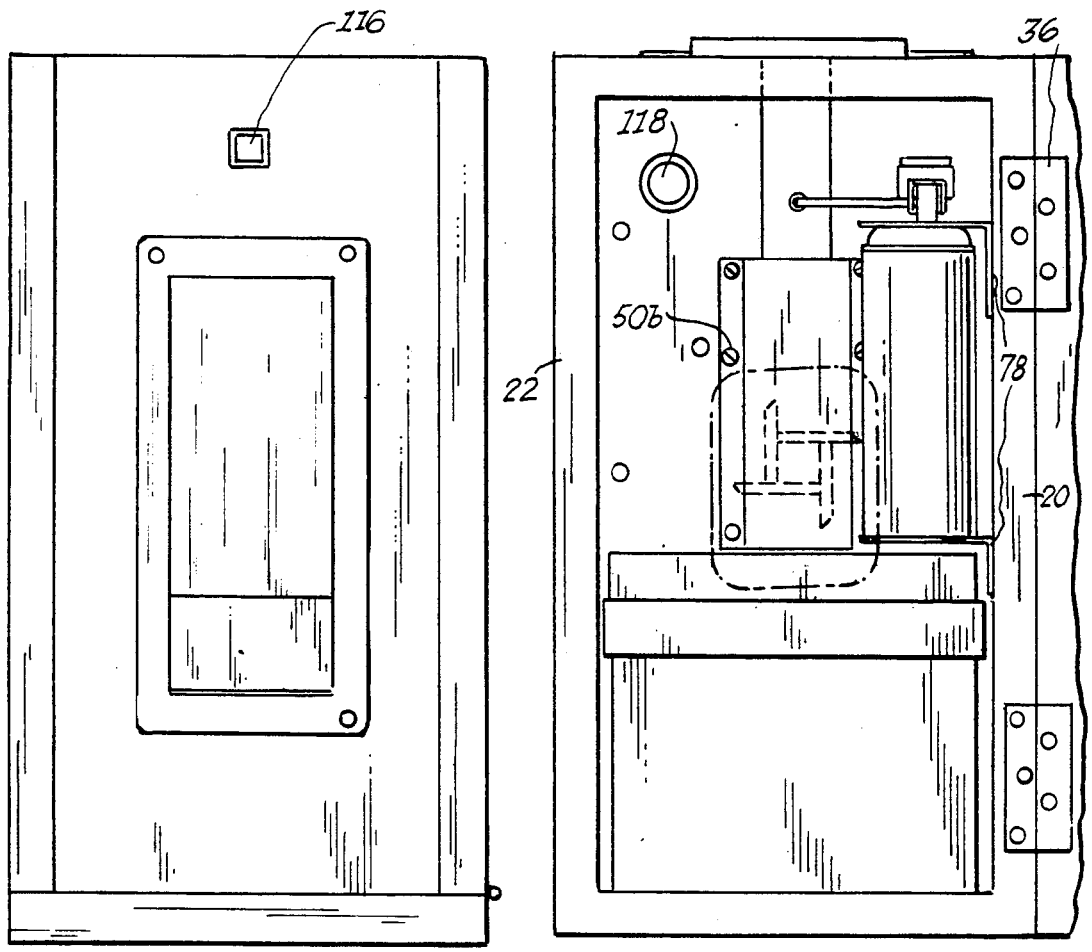
FIG. 3.
FIG. 2.
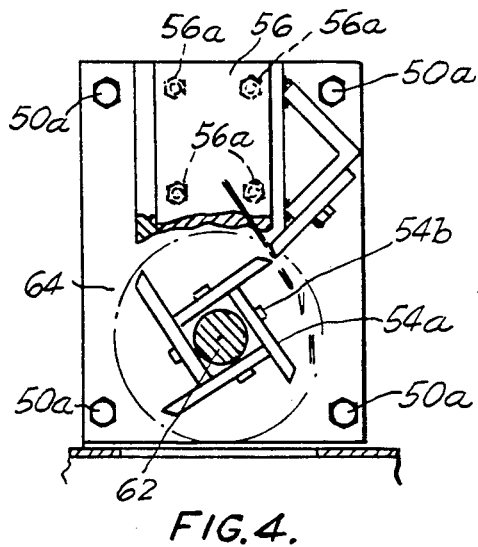
FIG. 4.
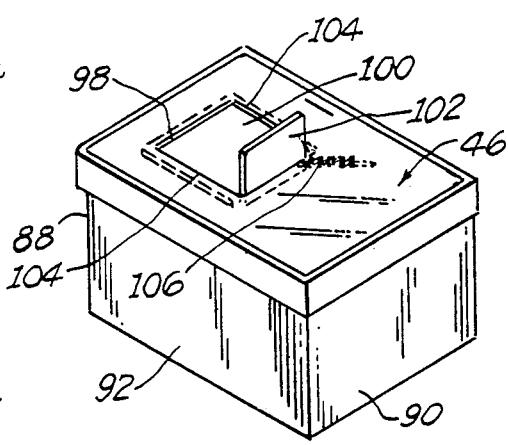
FIG. 6.

NEEDLE ELIMINATOR

BACKGROUND OF THE INVENTION

1. Field of the Invention

This invention relates generally to a machine for destroying medical waste, and more particularly, to a machine for destroying hypodermic needles and syringes to prevent reuse and depositing the waste in a self-contained safety container to eliminate human handling or contact with the needle components or body fluids thereon to prevent injury and reduce the spread of disease.

2. Description of the Prior Art

Devices for destroying medical syringes and needles are well known in the art. One example of such a device is the apparatus disclosed in U.S. Pat. No. 3,995,768 issued to Montalbano, et al.

The Montalbano patent discloses a cartridge arrangement for handling multiple syringes to be disposed of by a high speed cutter coupled to a motor operating in the range of 230 RPM. The syringes are fed into a chute between stationary and rotatable cutting members having serrations over a portion of their outer surface which form a tapered confronting surface so that the syringes are completely crushed prior to disposal in a removable and disposable liner or cardboard box.

Such a configuration has inherent disadvantages in that the high speed motor driven cutter produces a substantial amount of noise which may preclude its operation in certain areas of hospitals, nursing homes or doctors' offices. Moreover, the disposable liner does not provide an effective safety margin against inadvertent human contact with the disposed waste should some of the needles remain intact after the destruction process.

Therefore, there exists a need for a needle and syringe disposal apparatus which is capable of quiet operation and which includes a safety container which upon removal as a self-contained unit, continues to provide protection against inadvertent human contact with its contents.

SUMMARY OF THE INVENTION

In accordance with the present invention, there is provided a syringe and needle destruction machine for destroying, disinfecting and subsequently packaging the destroyed items in a self-contained safety container that prevents unauthorized access.

The invention comprises a compact, rigid rectangular main housing having an interior needle shearing chamber on one side, and a motor housing chamber on the other side, partitioned by at least one inner wall. Within the shearing chamber, there is disposed a means for shearing the syringes and needles into small pieces which is rotatably mounted on a motor output shaft extending through the inner wall to a high torque, low RPM motor (below 40 RPM), which is rigidly secured to the housing.

The shearing component comprises a plurality of planar shearing members when viewed parallel to the inner wall which taper at one end to form a shearing surface and which abuts adjacent shearing members at the other end when mounted on a hub member which is attached to the motor output shaft. The planar shearing members define a phantom circular boundary or path as they spin about the drive shaft axis and form a shearing surface against an angle-shaped adjustable shearing member having a lower leg tapered to a knife edge which is situated directly in relation to the above described "circle".

Surrounding the shearing component is a shearing housing which comprises a square tube feed member which is rigidly secured to the main housing inner wall by a planar base plate. On the outer edge of the square tube is an outer plate which has a hole therethrough so it can support the motor shaft in a pivot joint. These components are enclosed by a thin walled outer cover which is firmly anchored to the planar base plate. Extending vertically from the shearing housing is an elongated catch bin which is a hollow tubular member having a smaller perimeter than the shearing housing tube member so that it may be mounted therein. Deposit access tube abuts the top wall of the housing and is coincidentally disposed with an aperture defined in the top wall of the main housing to receive discarded needles and syringes for destruction.

A disinfecting device for the shearing housing is provided as an additional safety feature. The disinfecting device typically comprises a sprayable can of antiseptic such as "Lysol" which is rigidly secured to one of the housing side walls by a bracket assembly. The antiseptic spray is activated by a solenoid which is mounted against the main housing top wall in the motor chamber and which biases an arm extending therefrom through the inner wall and over the spray head of the antiseptic nozzle such that the spray head is pushed down to discharge a time controlled amount of antiseptic. Both the solenoid and shearing means drive motor are connected via a switch which is activated by sliding an access door in the main housing top wall disposed across the aperture directly above the elongated catch bin. The switch is configured so that when the access cover is moved through a half way open position, the solenoid is activated and an antiseptic is discharged into the cutter housing for a short period of less than a second. When the sliding access cover is in a fully open position, the timing circuit is closed and the articles to be destroyed are manually dispensed in the deposit access tube. As the cover returns by spring action towards the closed position, another short injection (less than a second) of antiseptic is discharged as the cover passes the half way position and upon the end of return travel, the slide safety switch is enabled and the motor is activated initiating the destruction process for a predetermined amount of time as set by a timer, typically ranging from three to 10 seconds.

A removable container for receiving the destroyed syringe and needle constituents is slidably mounted but securely locked in the main housing adjacent to and below the shear housing. A safety switch interlock which disables the device when the safety container is removed is provided to prevent inadvertently engaging the shear mechanism with the safety container removed. The safety container has a spring loaded and flanged normally closed top door which opens to reveal an aperture for passing the waste through as the safety container is moved into position beneath the shear housing causing the flange on the door to engage the exterior thereof. In this manner, when the safety container is pulled out of the main housing, the spring loaded top door snaps shut thereby precluding accidental contact with the waste contained therein. The container itself is a self-contained discardable unit which may include an outer marking such as "disposable or infectious waste" if desired.

It is an object of the present invention to provide a device for disposing of used syringes and needles in a safe manner to reduce the spread of disease and infection and decreases the volume of waste.

It is an additional object of the instant invention to provide a device for disposing of used syringes and needles which is compact in size.

It is still a further object of the instant invention to provide a device for disposing of used syringes and needles which operates with a minimum amount of noise.

It is another object of the present invention to provide a device for disposing of used syringes and needles which exhibits ease of operation and affords the user maximum safety.

In accordance with these and other objects which will become apparent hereinafter, the instant invention will now be described with particular reference to the accompanying drawings.

BRIEF DESCRIPTION OF THE DRAWINGS

FIG. 2 is a front elevational view of inside of the main housing.

FIG. 3 is a top plan view of the main housing.

FIG. 4 is a front cutaway view of the shear assembly.

FIG. 6 is a perspective view of the removable, disposable safety container.

DETAILED DESCRIPTION OF THE PREFERRED EMBODIMENT

Figure 1:
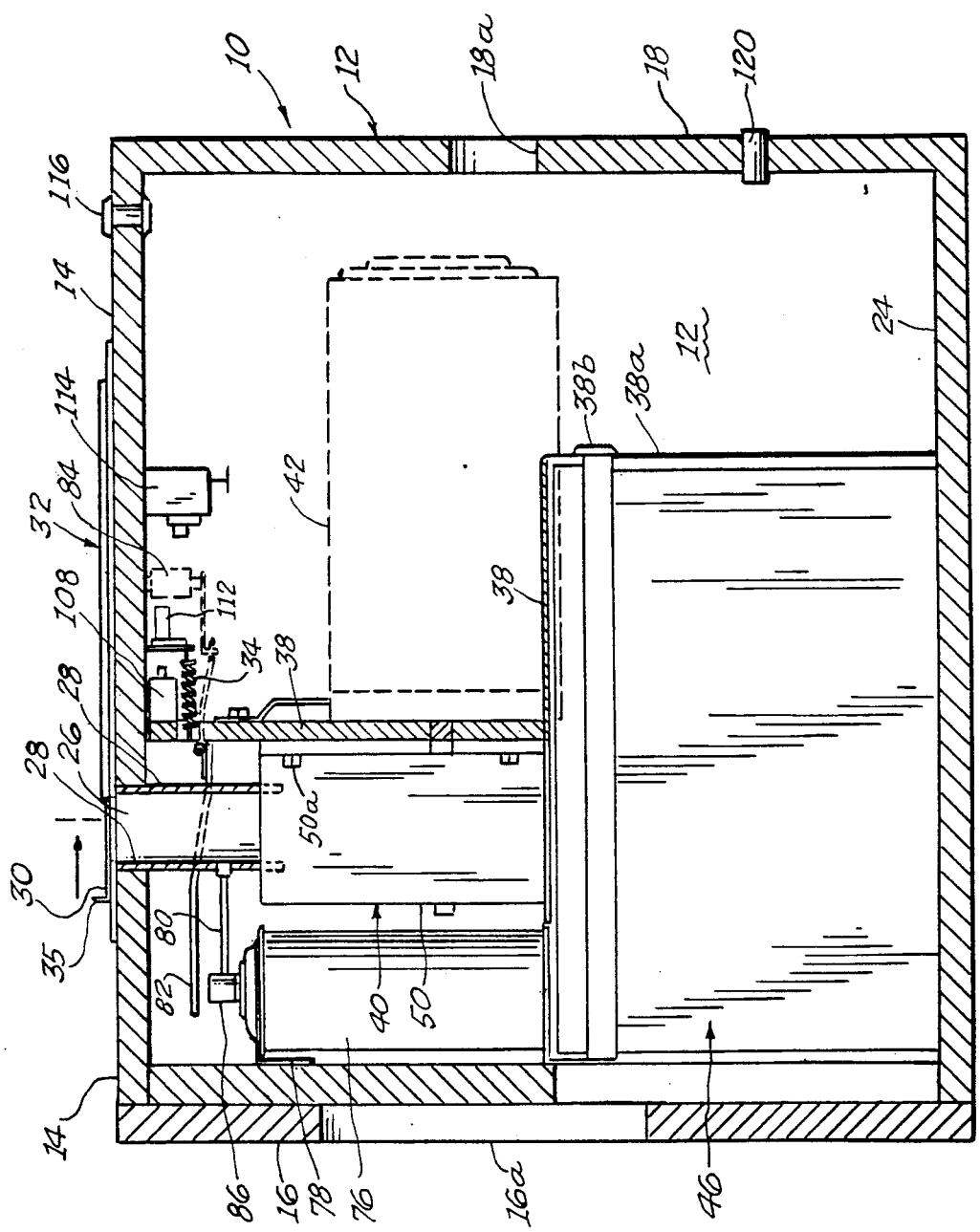
FIG. 1 is a side elevational view of through main housing of the invention.

With reference to the several views of the drawings, there is depicted a machine for destroying, disinfecting and storing used syringes and needles generally characterized by reference numeral 10. As a general reference to size, the main housing is approximately 16" long, 10" wide and 16" high.

FIG. 1 shows a side elevational view of housing 12 and its internal components which make up the invention. Housing 12 is a rigid box structure made of any suitable material such as wood or plastic with a cleanable exterior surface such as formica having a top wall 14, a door 16, a removable rear wall 18 with an air vent 18a, side walls 20 and 22, and bottom wall 24. Top wall 14 includes aperture 26 therethrough so that used syringes and needles may be manually deposited and passed into deposit access tube 28 for ultimate destruction below. Exterior housing access door 30 is slidably mounted in frame 32 contained within top wall 14, so that access door 30 covers aperture 26 as shown in FIGS. 1 and 3. A biasing spring 34 is provided to urge door 30 into a normally closed position. To facilitate easy opening of door 30, flange 35 of sufficient width is provided so that it may be easily grasped by a human hand. Door 16 is hingedly connected to hinges 36 to an adjacent side wall 20 such that full access to the interior of housing 12 is provided as shown in FIG. 2. Housing 12 further contains partial inner wall 38 which rigidly supports shear housing 40 and motor 42 to be more fully described hereinbelow. Wall 38a continues as a thin sheet of metal from upper wall 38 to create a four-sided surface abutting side walls 20 and 22, and bottom wall 24. Portions of wall surfaces 20, 22, 24 and 38a are sized to slidably receive safety container 46, discussed in greater detail hereinafter.

Figure 5:
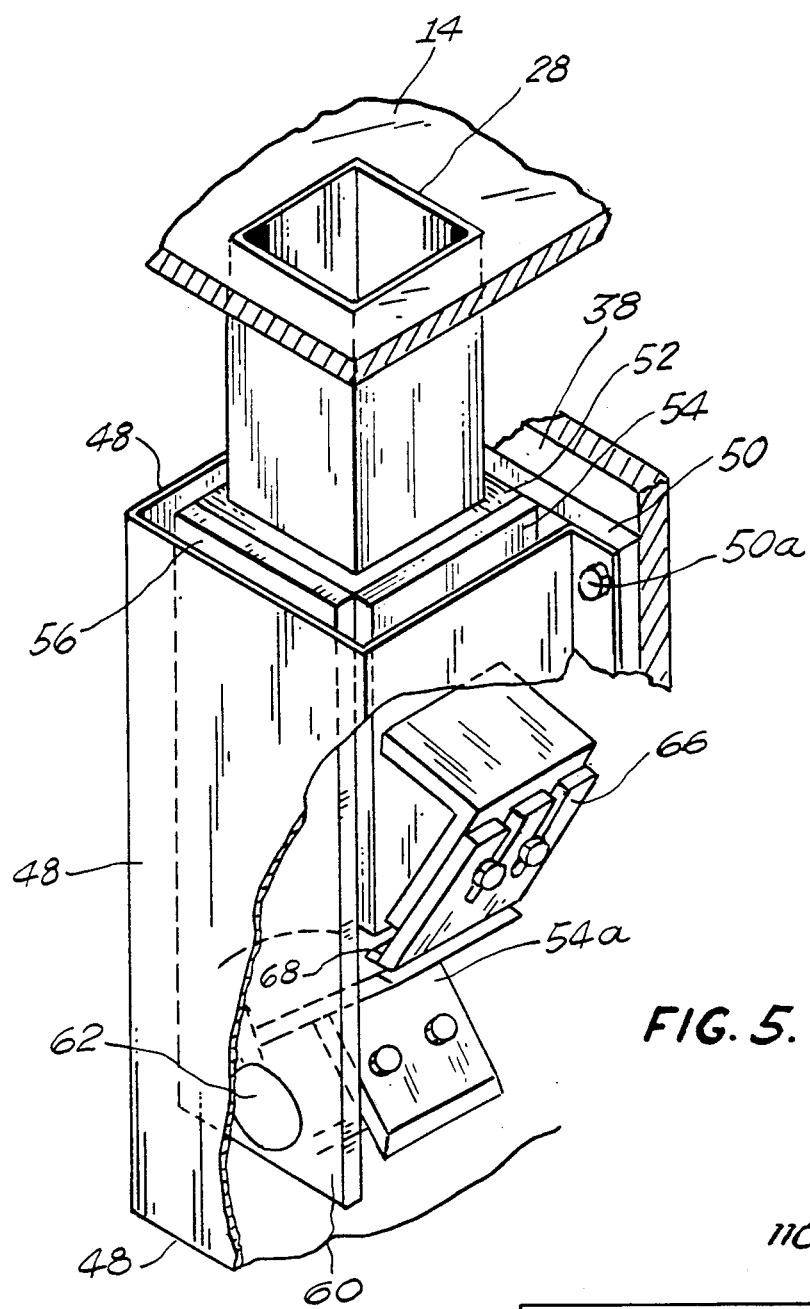
FIG. 5 is a perspective cutaway view of the shear assembly.

FIGS. 4 and 5 show detail of shear housing 40. Deposit access tube 28 is a square tube member which sits flush against the interior of housing top wall 14 and which is received within shear housing 40. Shear housing 40 comprises a relatively thin-walled outer cover 48 which is rigidly attached to mounting plate 50 which in turn is rigidly secured to inner wall 38. Deposit access tube 28 is received within one end of square tube member 52 which is additionally sized so that shear blade assembly 54 substantially across the lower end of tube 52 which has curved shape on the back and the front. Tube member 52 is rigidly secured to base plate 50 on one side and has a plate 56 attached on its other side, including an aperture for receiving the shear blade assembly shaft.

Shear blade assembly 54 comprises a plurality of planar shearing members 54a having tapered shearing edges 58 at one end. Shearing blades assembly 54 is removably mounted on hub member 60 which in turn is rigidly attached to output shaft 62 of motor 42. Shearing members 54a are oriented on planes transverse to partial inner wall 38 and define a phantom circular outer boundary path 64 when rotated on shaft 62. Adjustable angular shaped planar shearing member 66 is disposed adjacent to the lower end of tube member 52 and securely fastened thereto such that carbide shear edge 68 is perpendicular to phantom circular outer boundary 64 to form a confronting surface with shear blades 54a. Output shaft 62 is rotatably supported through partial inner wall 38 and within hole 58 of plate 56. When any of the individual shearing blades require service, access is available by removing shear housing thin-walled outer cover 48 by removing four bolts 50a, square tube member 52, and planar member 56 from base plate 50.

For quick disassembly and servicing shearing assembly, the following steps are taken:

1) Remove two screws 50b which releases outer cover 48;
2) Remove four screws 56a to release planar member 56;
3) To remove shear blades 54a, remove screws 54b. At this point, shear blade can be cleaned and sharpened;
4) To remove adjustable carbide blade 66, remove screw 66a. To adjust carbide blade 66, loosen screws 66a. Adjust to proper clearance with shear blades 54a, then tighten screws 66a.

Adjustments can only be made when shear assembly 40 is removed.

As shown in FIG. 1, motor 42 is rigidly secured to partial inner wall 38 with four nuts 50a on the opposite side. The motor is a conventional AC or DC (battery-rechargeable) type capable of transmitting high torque values to output shaft 62 while turning in the range of 37 RPM. This is a significant aspect of the invention since the high torque and relatively low rpm coupled with the novel shear design described above results in appreciably lower noise levels during operation, essential for hospital environments.

A pressurized canister for disinfecting shear housing 40 is located within housing 12 and comprises a typical aerosol spray can dispenser 76 containing an antiseptic or disinfectant such as "Lysol" attached to the interior of side wall 22 by bracket 78. Conduit 80 may be provided to direct the spray directly into access tube 28 if desired. The spray is activated by arm member 82 which passes through inner partial wall 38 and which is attached to solenoid 84. Solenoid 84 is secured to top wall 14 of housing 12. When solenoid 84 is energized, arm 80 is biased against spray head 86 of disinfectant can 76 for a period of less than one second which results in expending antiseptic into shear housing 40 surrounded by shield 50 via access tube 28.

FIG. 6 depicts a removable, disposable safety container 46 which is slidably mounted within housing 12 against wall 38a (FIG. 1) and electrical override safety switch 38b which prohibits turn on of the machine unless a safety container is pressed against switch 38b. Safety container 46 is substantially rectangular having top wall 86, front wall 88, rear wall 90, side walls 92 and 94, and bottom wall 96. Top wall 86 has aperture 98 therethrough which is covered by normally closed sliding cover 100. Sliding cover 100 has flange 102 disposed at right angles thereto on the side of aperture 98 closer to rear wall 90. Sliding cover 100 is disposed in side rails 104 and engages tension spring 106 which pulls sliding cover 100 toward rear wall 90 such that cover 100 is in a normally closed position when safety container 46 is removed from housing 12. When safety container 46 is inserted into housing 12 with rear wall 90 facing housing wall 38a, flange 102 is forced against outer cover 48 of shear housing 40 thereby forcing sliding cover 100 to slide within side rails 104 toward front wall 88 so that aperture 98 is completely revealed when safety container 46 is fully installed within housing 12. Conversely, upon removing safety container 46 from housing 12 when filled with destroyed needles and syringes, sliding cover 100 will automatically snap shut under tension from spring 106 thus eliminating any chance of inadvertent contact between the operator and contents in safety container 46. Safety container 46 and the waste contained therein can subsequently be discarded as an integral unit, and is constructed of a low cost plastic, moisture proof and suitable as a throw away.

Figure 7:
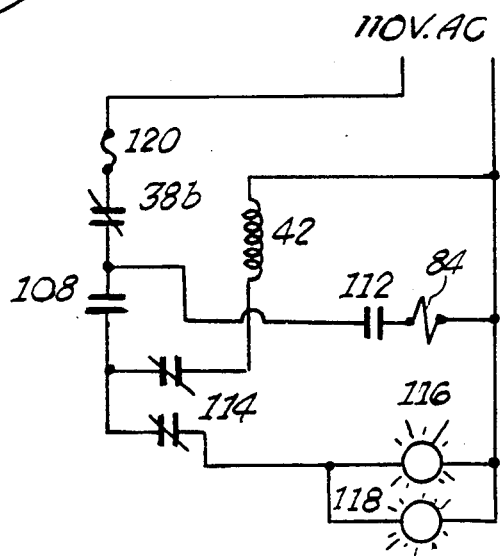
FIG. 7 is a circuit diagram showing the various switches used in the invention.

The circuit diagram illustrated in FIG. 7 discloses the electrical operation of the invention. Slide safety switch 108 is disposed at the end of sliding access door 30 proximate to front wall 16 Of housing 12. Switch 108 disables motor 42 when sliding door 30 is not in a fully closed position as a safety precaution. Likewise, access tube interlock switch 38b disables the entire circuit when safety container 46 is not fully installed with rear wall in operable association with housing inner wall 38a. Spray roller switch 112 is situated along the travel of sliding door 30 such that it is tripped when sliding door 30 travels past its half way open point. At this time, solenoid 84 is energized forcing arm 82 downward against spray cap 86 of can 76 for a period of less than one second so that the shear housing is disinfected as described above. When door 30 is slid into a fully opened position, cycle timing circuit 114 is closed. At this time, the needles and syringes to be destroyed are manually dropped into access tube 28 so that they may freely pass into tube member 52 directly above shear blades 54a. Sliding door 30 is slid forward toward front wall 16 of housing 12 tripping spray roller switch 112 again which results in an additional less than one second injection of disinfectant as described above. When sliding door 30 is fully retracted, slide safety switch 108 is closed and motor 42 is engaged for a period set by cycle timing circuit 114, typically ranging from three to 10 seconds. When motor 42 is in operation, blades 54a force the needles and syringes to be destroyed against flat carbide edge 68 of adjustable shear member 66 (which acts like a bed knife). In this manner, the waste is broken up into small pieces which drop through aperture 98 in top wall 86 of safety container 46 into the cavity defined therein. During operation of apparatus 10, power light 116 disposed in top wall 14 of housing 12, and access tube light 118 disposed in partial inner wall 38 of housing 12, are illuminated. A 15 amp circuit breaker 120 is provided and may be disposed in wall 18 of housing 12 to facilitate easy access thereto.

The instant invention has been shown and described herein in what is considered to be the most practical and preferred embodiment. It is recognized, however, that departures may be made therefrom within the scope of the invention and that obvious modifications will occur to a person skilled in the art.

What I claim Is:

1. An apparatus for destroying hypodermic needles and syringes comprising:

a main housing having a top wall, a front wall, a rear wall, two side walls, a bottom wall and at least one inner wall defining multiple cavities therein, said top wall defining an aperture therethrough and having means for slidably mounting an access door across said aperture, said front wall having means for providing access to the interior of said housing;

a motor having an output shaft, said motor rigidly attached to said inner wall;

means for shearing said needles and syringes into unusable parts for disposal attached to said motor output shaft;

a cutter housing surrounding said means for shearing and rigidly attached to said housing inner wall, said cutter housing having open top and bottom ends;

an elongated deposit access tube for receiving and guide said needles and syringes into said cutter housing extending vertically from within said cutter housing to said main housing top wall and aligned with said main housing top wall aperture, said deposit access tube rigidly attached to said cutter housing;

a removable safety container having a spring loaded top lid in a normally closed position, said safety container configured to slidably mount within said main housing such that said top lid is opened to reveal an aperture when said safety container is disposed in said main housing below and adjacent to said cutter housing;

means for disinfecting said cutter housing disposed adjacent thereto and rigidly secured to said main housing; and means for activating said means for shearing and means for disinfecting attached to said access door across said aperture in said top wall of said main housing whereby said means for disinfecting inject disinfectant into said shear housing as said access door is slid from a closed to an open position, said needles and syringes are deposited through said aperture and said main housing top wall into said catch bin and said access door is returned to said closed position at which time said motor is enabled causing said means for shearing to destroy said needles and syringes which subsequently pass from said cutter housing into said safety container.

2. The apparatus recited in claim 1, wherein said means for shearing comprise:

a hub member rotatably mounted on said motor output shaft;

a plurality of planar shearing members having tapered shearing surfaces, said shearing members disposed on said hub member transverse to and within said cutter housing; and an adjustable planar shearing member having a shearing surface disposed along the circular phantom path defined by rotating said hub mounted shearing members.

3. The apparatus recited in claim 1, wherein said cutter housing comprises:

a planar inner base plate secured to said main housing inner wall;

a square tube member attached to said inner base plate for guiding said needles and syringes from said deposit access tube to said means for shearing;

a planar outer member attached to said square tube at one end and defining an aperture therethrough at its other end for accepting said motor output shaft; and a thin walled outer cover overlapping said square tube member and said planar outer member to form a housing boundary, said outer cover rigidly secured to said inner base plate.

4. The apparatus recited in claim 1, wherein said means for providing access to said housing comprises said forward wall hingedly connected to one of said adjacent side walls.

5. The apparatus recited in claim 1, wherein said means for disinfecting comprise:

a can of disinfectant having a spray head;

a bracket member for supporting said can of disinfectant, said bracket member rigidly secured to one of said side walls inside said main housing;

a solenoid connected to said means for activating and rigidly attached to said main housing; and an elongated arm member attached to said solenoid and disposed above and adjacent to said spray head of said can of disinfectant whereby said solenoid urges said arm down and against its spray head upon activation of said solenoid.

6. The apparatus recited in claim 1, further comprising a power light disposed on said top wall of said housing to indicate when said apparatus is operational.

7. The apparatus recited in claim 1, further comprising means for locking said front wall of said main housing.

8. An apparatus for destroying hypodermic needles and syringes, comprising:

a main housing having a top wall, a front wall, a rear wall, two side walls, a bottom wall and at least one inner wall defining multiple cavities therein, said top wall defining an aperture therethrough and having means for slidably mounting an access door across said aperture, said front wall hingedly connected to an adjacent side wall to provide access to the interior of said main housing;

a motor having an output shaft, said motor rigidly attached to said inner wall;

means for shearing said needles and syringes into unusable parts for disposal, said means for shearing comprise a hub member rotatably mounted on said motor output shaft, a plurality of planar shearing members having tapered shearing surfaces, said shearing members disposed on said hub member on planes transverse to said main housing inner wall, and an adjustable planar shearing member having a tapered shearing surface disposed tangent to the phantom circular path defined by rotating said hub mounted shearing members about said motor shaft;

a shear housing surrounding said means for shearing and rigidly attached to said main housing inner wall, said shear housing having open top and bottom ends and comprising, a planar inner base plate rigidly secured to said main housing inner wall, a square tube member attached to said base plate and extending vertically for receiving said syringes and needles, a planar outer member attached to the outer periphery of said square tube member at one end and defining an aperture therethrough at its other end for accepting said motor output shaft, and a thin walled outer cover overlapping said square tube member and said planar outer member to form a cutter housing boundary, said outer cover rigidly secured to said inner base plate;

an elongated deposit access tube for receiving and guiding said needles and syringes into said shear housing extending vertically from within said shear housing square tube member to said main housing top wall and aligned with said main housing top wall aperture, said catch bin rigidly attached to said main housing top wall;

a removable safety container having a spring loaded top lid in a normally closed position, said safety container configured to slidably mount within said main housing such that said top lid is opened to reveal an aperture when said safety container is disposed in said main housing below and adjacent to said shear housing;

means for disinfecting said shear housing disposed adjacent thereto and rigidly secured to said main housing, said means for disinfecting comprising, a can of disinfectant having a spray head, a bracket member for supporting said can of disinfectant, said bracket member rigidly secured to one of said side walls of said housing, a solenoid rigidly attached to said main housing, and an elongated arm member attached to said solenoid and disposed above and adjacent to said spray head of said can of disinfectant whereby said solenoid urges said arm down and against its spray head upon activation of said solenoid; and means for activating said means for shearing and means for disinfecting attached to said axis door across said aperture and said top wall of said main housing whereby said means for disinfecting injects disinfectant into said cutter housing as said access door is slid from a closed to an open position, said needles and syringes are deposited through said aperture and said housing top wall into said deposit access tube and said access door is returned to said closed position at which time said motor is enabled causing said means for hearing to destroy said needles and syringes which subsequently pass from said cutter housing into said safety container.

* * * * *